United States Patent
Kreyenschmidt et al.

(10) Patent No.: US 7,960,177 B2
(45) Date of Patent: Jun. 14, 2011

(54) SET OF CALIBRATION STANDARDS

(75) Inventors: Martin Kreyenschmidt, Lohne (DE); Christian Mans, Steinfurt (DE); Stephanie Hanning, Havixbeck (DE)

(73) Assignee: Fachhochschule Münster, Münster (DE)

( * ) Notice: Subject to any disclaimer, the term of this patent is extended or adjusted under 35 U.S.C. 154(b) by 441 days.

(21) Appl. No.: 12/093,399

(22) PCT Filed: Nov. 10, 2006

(86) PCT No.: PCT/DE2006/001970
§ 371 (c)(1), (2), (4) Date: May 12, 2008

(87) PCT Pub. No.: WO2007/056977
PCT Pub. Date: May 24, 2007

(65) Prior Publication Data
US 2008/0233652 A1    Sep. 25, 2008

(30) Foreign Application Priority Data
Nov. 15, 2005   (DE) .................. 10 2005 054 443

(51) Int. Cl.
*G01N 31/00* (2006.01)
*G01N 33/20* (2006.01)

(52) U.S. Cl. .................. 436/8; 436/73; 436/77; 436/81; 436/83; 436/124; 436/174; 73/1.01; 73/1.03; 419/67

(58) Field of Classification Search .............. 436/8, 73, 436/77, 81, 83, 124, 172, 173, 174; 73/1.01, 73/1.03; 72/253.1; 419/67
See application file for complete search history.

(56) References Cited

U.S. PATENT DOCUMENTS
7,197,110 B2 *   3/2007  Riess et al. .................. 378/45

FOREIGN PATENT DOCUMENTS
DE   27 16 689 A1   10/1978
DE   197 28 930 A1   1/1999
JP   2004-257809 A   9/2004

OTHER PUBLICATIONS

Miyagi et al. (abstract) "Development of Reference Materials for the Determination of Hazardous Elements in Plastics". JFE Giho, vol. 13, pp. 82-86.*

Nakano et al., Preparation of calibrating standards for x-ray fluorescence spectrometry of trace metals in platics, X-Ray Spectrometry, 2003, 32: pp. 452-457.
Lamberty et al., Collaborative study to improve the quality control of trace element determinations in polymers . . . , Fresenius J Anal Chem, 2001, S.811-818.
Quevauviller, Certified reference materials for the quality control of inorganic analyses of manufactured . . . , Trends in analytical chemistry, vol. 20, No. 8, 2001, pp. 446-456.
Kempenaers et al., The use of LA-ICP-MS for the characterization of the micro-heterogeneity of heavy metals in BCR CRM 680, J. Anal. At. Spectrom, 2001,16, pp. 1006-1011.
Kempenaers et al., Micro-heterogeneity study of trace elements in 6CR CRM 680 by means of synchrotron micro-XRF, Fresenius J. Anal. Chem., 2001, 369, pp. 733-737.
Dzubay et al., Polymer Films as Calibration Standards for X-Ray Fluorescence Analysis, Advances in X-ray Analysis, 20,1977, pp. 411-421.
Dzubay et al., Polymer Film Standards for X-Ray Fluorescence Spectrometers, J. Trace and Microprobe Techniques, 5,,4,1987-1988, pp. 327-341.
Bichinho et al., Determination of catalyst metal residues in polymers by X-ray fluorescence, Spectrochimica Acta, Part B, 60, 2005, pp. 599-604.
Bertucci et al., Analyse de traces dens le PVDF par fluorescence X et ICP-MS avec ablation laser, Journal de Physique IV, vol. 6, 1996, C4-853-862.
Nakano et al., Development of Calibrating Standards for X-Ray Fluorescence Spectrometry of Trace Metals in Platics, Adv. X-Ray. Chem. Anal., Japan 35, 2004, pp. 101-112.
Chiba et al., High-Sensitive and Nondestrictive Determination of Trace Heavy Toxic Elements in Plastics by Using Energy . . . , Adv. X-Ray, Chem. Anal. Japan 35, 2004, pp. 113-124.
Nakano et al., Prepareation of Calibrating Standard Materials for the Determination of Trace Elements in Plastics, Rigaku, January, 36, 2006, pp. 16-19.
Ochi et al., Analysis of Cd and Pb in Plastics Using Energy Dispersive X-ray (EDX) Fluorescence Spectrometer, Shimadzu, 2004, vol. 60, pp. 137-145.

* cited by examiner

*Primary Examiner* — Maureen M Wallenhorst
(74) *Attorney, Agent, or Firm* — Jason D. Voight

(57) ABSTRACT

A standard calibration set having at least three calibration standards. Each standard is a molded article made of a thermoplastic polymer which contains the elements Cd, Cr, Pb, Hg and Br, with the Cr:Pb:Hg:Br:Cd ratio being different in each of the three calibration standards. Further disclosed is a method for manufacturing the calibration standards and their use in X-ray fluorescence analysis.

20 Claims, No Drawings

SET OF CALIBRATION STANDARDS

This is the National Stage of International Application PCT/DE2006/001970, filed Nov. 10, 2006.

The present invention relates to a standard calibration set comprising at least three calibration standards that consist of a molded article made of a thermoplastic polymer which contains the elements Cd, Cr, Pb, Hg and Br, with the Cr:Pb:Hg:Br:Cd weight ratio being different in each of the three calibration standards, and to a method for manufacturing said calibration standards and their use in X-ray fluorescence analysis, laser ablation ICP and laser-induced plasma spectroscopy (LIPS).

Electric and electronic devices often contain contaminants that are harmful to the environment and health and have to be recycled or disposed of in a suitable form. For this reason, there exist legal provisions to reduce the damage to the environment and health caused by electric and electronic devices.

For the manufacturers and disposal companies of electric and electronic devices it is therefore important to be able to analyze the content of contaminants by using a method that is as advantageous as possible. In addition, polymer manufacturers have to rely on a method in order to be able to analyze certain marker elements in plastics that are added for product identification purposes. Therefore, one has to rely on a fast and economical multi-element analytical method that make as little demands on sample preparation as possible.

The analytical methods proposed so far in the prior art are only partly suitable for those demands. For example, plastics can be tested for their content of elements only after extensive acid hydrolysis by means of inductively coupled plasma mass spectrometry (ICP-MS) or inductively coupled plasma optical emission spectroscopy (ICP-OES) or atom absorption spectrometry (AAS).

In the prior art, there is also evidence of problems regarding the analysis of the regulated elements chromium (VI) and bromine. For example, FT-IR spectroscopy (Fourier transform infrared spectroscopy) or GC-MS (gas chromatography-mass spectrometry) is proposed as an analytical technique for the analysis of polybromated biphenylene and polybromated diphenylethers. For the quantitative determination of Cr (VI), UV-VIS spectroscopy (photometric measurement in the UV and visible light range) is recommended.

Identification of bromated flame retardants by means of FT-IR spectroscopy is also known in the prior art. If bromated flame retardants are present in a plastic, one should be able to determine them in high concentrations exceeding 5% by means of FT-IR spectroscopy using bands in the fingerprint range from 1,000 to 1,500 cm$^{-1}$. However, this method cannot be used for a quantitative analysis.

In another method for the quantitative and qualitative determination of bromated flame retardants in polymer housings known in the prior art, the flame retardants are extracted with isopropanol in an ultrasonic bath and subsequently determined by means of HPLC-UV.

Determination by means of Cr (VI) using ion chromatography is also known. In particular, it is to be noted that maintaining the appropriate pH for the analysis is of great importance.

What all of the techniques described above have in common is that they can only be performed by specially trained staff. In addition, the need for having to have many different analytical devices at your disposal in a lab environment raises the costs significantly, which directly affects the product costs.

It is thus desirable to develop an analytical method which permits the characterization of materials in accordance with the required limits in a timely manner without using extensive disintegration methods.

The development of a method using X-ray fluorescence analysis to determine the regulated substances would have the advantage over the above mentioned methods that it eliminates extensive sample preparation facilitating an economical analysis in a timely manner. Although this method only allows to make a statement regarding the element content per se rather than facilitating the distinction between Cr (III) and Cr (VI) or the characterization of different bromated flame retardants, a statement regarding the total content of the limited elements often suffices in practice.

A general problem of all types of X-ray fluorescence devices is that this method is a relative method. A previous calibration using external standards—which have to have the same matrix and sample geometry as the sample to be tested—is absolutely necessary to make reliable quantitative statements.

In order to be able to utilize X-ray fluorescence analysis for the analysis of electric and electronic devices and their components, the development of respective standard calibration materials is very important.

For this reason, Nakano et al. propose calibration materials that are prepared by introducing metal-organic contaminants into liquid polyester or polyurethane blends (see Nakano et al., *"Preparation of calibrating standards for x-ray fluorescence spectrometry of trace metals in plastics"*, X-Ray Spectrom. 2003, 32, 452-457). However, the calibration materials are not suited to be used as standard calibration materials for the determination of contaminants in electric and electronic devices, since both the suggested amounts of contaminants and the suggested polymer matrix are unsuitable.

Furthermore, Lamberty et al. describe calibration materials that are prepared by blending powdery contaminants with polyethylene (see Lamberty et al., *"Collaborative study to improve the quality control of trace element determination"*, Fresenius J. Anal. Chem., 2001, 370, 811-818). However, the calibration materials are not suited to be used as standard calibration materials for the determination of contaminants in electric and electronic devices, since both the suggested amounts of contaminants and the suggested polymer matrix are unsuitable. In addition, the distribution of the contaminants is not sufficiently homogeneous and the powder granules used as calibration material are not advantageous to handle. Furthermore, master batch standards are prepared by dilution and do not comply with the sample geometry of the anticipated samples.

Thus, the calibration materials known so far are not suitable to be used as advantageous large-scale standard calibration materials for the determination of contaminants, in particular in electric and electronic devices.

It is thus an object of the present invention to provide standard calibration materials that can be advantageously used to determine contaminants in polymers, in particular contaminants present in electric and electronic devices, by means of analytical methods such as X-ray fluorescence analysis. Moreover, a calibration should be possible even when the electric and electronic articles to be tested do not consist of unmixed plastics, but, for example, contain blends of various plastics.

Another object of the present invention is to provide standard calibration materials that can be easily and advantageously handled to calibrate suitable analytical devices such as X-ray fluorescence devices.

Another object of the present invention is to provide standard calibration materials comprising a highly homogenous distribution of the contaminants in order to facilitate calibration with an advantageous accuracy of error.

Another object of the present invention is to provide standard calibration materials that allow the determination of contaminants in polymers by means of X-ray fluorescence analysis and laser ablation ICP (spectroscopic method using an inductively coupled plasma as ion or excitation source in conjunction with a laser ablation unit used as sample injection system) and include common fillers such as flame retardants or pigments. In addition, determination by means of laser-induced plasma spectroscopy (LIPS) should also be possible.

Another object of the present invention is to provide a method for manufacturing standard calibration materials that allow the determination of contaminants in polymers by means of X-ray fluorescence analysis.

Another object of the present invention is to provide a method for manufacturing standard calibration materials that allow the determination of contaminants in polymers by means of laser ablation ICP.

Another object of the present invention is to provide a method for manufacturing standard calibration materials that allow the determination of contaminants in polymers by means of LIPS.

A particular object of the present invention is to provide a method that facilitates the advantageous introduction of contaminants during manufacture without contaminating the environment and/or causing any damage to health.

A final object of the present invention is to provide a method that allows the advantageously homogeneous introduction of contaminants by means of an economical manufacturing process.

The objects of the present invention may be solved by the standard calibration sets and methods for their manufacture described in the claims.

Thus, the subject of the present invention is a standard calibration set comprising at least three calibration standards that consist of a molded article made of a thermoplastic polymer which contains the elements Cd, Cr, Pb, Hg and Br, with the Cr:Pb:Hg:Br:Cd weight ratio being different in each of the three calibration standards.

Another subject of the present invention is the use of a standard set of the present invention for the calibration of a device used in X-ray fluorescence analysis. Another subject of the present invention is the use of a standard set of the present invention for the calibration of laser ablation ICP-MS, laser ablation ICP-OES or LIPS devices.

A final subject of the present invention is a method for manufacturing a calibration standard consisting of a molded article made of a thermoplastic polymer which contains the elements Cd, Cr, Pb, Hg and Br, comprising the steps of
1) blending a powder containing the elements Cd, Cr, Pb, Hg and a liquid or powder containing the element Br with a dispersing agent,
2) blending the dispersion resulting from step 1 with the particulate thermoplastic polymer,
3) extruding the polymer of step 2 to preferably form granules.

In the present invention, substances or elements are often presented in their chemical short forms, which have the following meaning:
Al Aluminum
As Arsenic
Ba Barium
Br Bromine
Ca Calcium
Cd Cadmium
Co Cobalt
Cr Chromium
Cu Copper
Fe Iron
Hg Mercury
K Potassium
Mg Magnesium
Na Sodium
Ni Nickel
Pb Lead
S Sulfur
Sb Antimony
Se Selenium
Si Silicon
Sn Tin The term "standard calibration set", as it is used herein, means three or more calibration standards.

A calibration standard comprises a molded article made of a thermoplastic polymer. This molded article contains defined amounts of contaminants.

Essential contaminants are the elements Cd, Cr, Hg, Pb and Br. If necessary, the elements As or Se, Ni or Co may be contained as further contaminants in a calibration standard.

In this embodiment, the amount of As ranges commonly between 1 ppm and 1 weight percent, preferably between 10 ppm and 5,000 ppm, more preferably between 50 and 500 ppm. The amount of selenium ranges commonly between 0.1 ppm and 3,000 ppm, preferably between 1 ppm and 1,000 ppm, more preferably between 10 ppm and 500 ppm. The amount of Ni and Co ranges commonly between 0.1 ppm and 5,000 ppm, preferably between 1 ppm and 2,000 ppm, more preferably between 10 ppm and 500 ppm.

In a preferred embodiment, the calibration standards contain only the above mentioned contaminants, in particular only Cd, Cr, Hg, Pb and Br.

The term "thermoplastic polymer", as it is used herein, means a polymer which remains thermoplastic if it is repeatedly heated and cooled within the temperature range typical for the processing of this material. The term "thermoplastic" means in particular the property of the polymer to soften when heated and solidify when cooled within a temperature range of 60° C. to 400° C., preferably of 60° C. to 300° C. In addition, in the softened state, the thermoplastic polymer can be repeatedly molded into molded articles (e.g. molded parts or extrudates) by extrusion.

Examples of suitable thermoplastic polymers are polyethylene (PE), polypropylene (PP), polystyrene (PS), acrylonitrile butadiene styrene (ABS), styrene acrylonitrile (SAN), polyamides (PA), polycarbonate (PC), polyvinylchloride (PVC), polyethylene terephthalate (PET), polyether ether ketone (PEEK), polybutylene terephthalate (PBT), poly(2,6-dimethyl-1,4-oxyphenylene) (PPE), chlorinated PE, polymethylstyrene-co-acrylonitrile (MeSAN) or thermoplastic polyurethane (TPU). Further examples are polymethylmethacrylate (PMMA), polyoxymethylene (POM), polybutylene terephthalate (PBT) and acrylonitrile styrene acrylic ester (ASA).

Thermoplastic polymers that are preferably used are polyethylene (PE), polypropylene (PP), polystyrene (PS), acrylonitrile butadiene styrene (ABS), styrene acrylonitrile (SAN), polyamides (PA), polycarbonate (PC) or polyvinylchloride (PVC). Additional preferred thermoplastic polymers are polymethylmethacrylate (PMMA) and polyoxymethylene (POM).

In particular, ABS and/or PC are used as thermoplastic polymers.

In general, the term "thermoplastic polymer", as it is used herein, also comprises any blend consisting of two or more of the above mentioned polymers. Preferably, the blends of the present invention are plastic alloys distributed on a molecular basis or dispersed microscopically.

Preferred Blends are:

ASA and PC, with the content of ASA usually being from 10 to 90 weight percent, preferably from 15 to 60 weight percent.

ABS and PC, with the content of ABS usually being from 5 to 90 weight percent, preferably from 55 to 85 weight percent, in particular 80 weight percent.

ABS and PA, with the content of ABS usually being from 5 to 90 weight percent, preferably from 20 to 80 weight percent.

PBT and ASA, with the content of PBT usually being from 2 to 95 weight percent, preferably from 10 to 80 weight percent.

PVC and ABS, with the content of PVC usually being from 5 to 95 weight percent, preferably from 10 to 85 weight percent.

PS and PPE, with the content of PS usually being from 5 to 70 weight percent, preferably from 10 to 60 weight percent.

PVC and MeSAN, with the content of PVC usually being from 5 to 90 weight percent, preferably from 10 to 80 weight percent.

PVC and (optionally chlorinated) PE, with the content of PVC usually being from 5 to 90 weight percent, preferably from 10 to 80 weight percent.

ABS and PUR, with the content of ABS usually being from 5 to 90 weight percent, preferably from 20 to 85 weight percent, in particular 70 weight percent.

The standard calibration set of the present invention comprises a first, second and third calibration standard.

The first calibration standard includes a certain Cr:Pb:Hg:Br:Cd weight ratio. The second and third calibration standards also include a certain Cr:Pb:Hg:Br:Cd weight ratio. In each of the three calibration standards the Cr:Pb:Hg:Br:Cd weight ratio is different.

The term "weight ratio", as it is used herein, means the ratio of the weight amounts of chromium atoms, lead atoms, mercury atoms, bromine atoms and cadmium atoms.

Preferably, not only the total Cr:Pb:Hg:Br:Cd weight ratio is different, but also the individual ratio of each calibration standard.

Preferably, each of the calibration standards has a different Cr:Pb weight ratio. In addition, each of the calibration standards has a different Cr:Hg weight ratio. Moreover, each of the calibration standards has a different Cr:Br weight ratio. Furthermore, each of the calibration standards has a different Cr:Cd weight ratio.

In addition, each of the calibration standards has a different Pb:Hg weight ratio. Moreover, each of the calibration standards has a different Pb:Br weight ratio. Furthermore, each of the calibration standards has a different Pb:Cd weight ratio.

In addition, each of the calibration standards has a different Hg:Br weight ratio. Furthermore, each of the calibration standards has a different Hg:Cd weight ratio.

In a preferred embodiment, each of the calibration standards contains at least one of the elements Cr, Pb, Hg and Br in an amount of 0.1 to 500 ppm and at least one of the elements Cr, Pb, Hg and Br in an amount of more than 500 ppm to 5,000 ppm, preferably 500 ppm to 2,000 ppm, based on the total weight of the polymer. In addition, in this preferred embodiment at least one calibration standard contains Cd in an amount of 0.1 to 50 ppm and at least one calibration standard contains Cd in an amount of more than 50 ppm to 1,000 ppm, preferably 50 ppm to 200 ppm, based on the total weight of the polymer.

The amount of a contaminant given in ppm relates to the weight percent of the respective element in the polymer matrix, but not to the weight of the administration form (e.g. oxide, sulfate, etc.) of the contaminant. Therefore, a value of 500 ppm Cr means that 500 ppm Cr atoms are contained in the polymer matrix rather than, for example, 500 ppm chromium oxide.

Apart from the above described first, second and third calibration standards, the standard calibration set of the present invention may also include further calibration standards.

In a preferred embodiment, the standard calibration set comprises at least 2n+2 calibration standards, with n presenting the number of elements to be calibrated.

It is advantageous if all calibration standards being part of the standard calibration set contain different amounts of the contaminants.

It is further advantageous if the Cr:Pb:Hg:Br:Cd ratio in the individual calibration standards is different. This means that it is generally advantageous if the individual calibration standards are not prepared by "dilution" of a master batch.

Apart from the calibration standards described so far, the standard calibration set of the present invention may additionally include a blank calibration standard. This blank calibration standard is a molded article made of a thermoplastic polymer containing no contaminants.

Table 1 below illustrates the amounts of contaminants contained in a preferred standard calibration set comprising 4 calibration standards and, if necessary, a blank calibration standard.

TABLE 1

| Calibration standard | Br [ppm] | Cd [ppm] | Cr [ppm] | Hg [ppm] | Pb [ppm] |
|---|---|---|---|---|---|
| 1 | 0-500 | 0-500 | 500-1,000 | 0-500 | 500-1,000 |
| 2 | 500-1,000 | 0-500 | 0-500 | 500-1,000 | 0-500 |
| 3 | 500-1,000 | 500-1,000 | 0-500 | 0-500 | 500-1,000 |
| 4 | 0-500 | 500-1,000 | 500-1,000 | 0-500 | 0-500 |
| Blank | 0 | 0 | 0 | 0 | 0 |

Table 2 below illustrates the amounts of contaminants contained in a preferred standard calibration set comprising 8 calibration standards and, if necessary, a blank calibration standard.

TABLE 2

| Calibration standard | Cr [ppm] | Br [ppm] | Cd [ppm] | Hg [ppm] | Pb [ppm] |
|---|---|---|---|---|---|
| Blank | 0 | 0 | 0 | 0 | 0 |
| 1 | 50-150 | 400-600 | 150-250 | 1-25 | 400-600 |
| 2 | 1-25 | 1000-1,500 | 50-150 | 20-80 | 50-150 |
| 3 | 20-80 | 1-25 | 20-80 | 50-150 | 1000-1,500 |

TABLE 2-continued

| Calibration standard | Cr [ppm] | Br [ppm] | Cd [ppm] | Hg [ppm] | Pb [ppm] |
|---|---|---|---|---|---|
| 4 | 1000-1,500 | 50-150 | 150-250 | 400-600 | 1-25 |
| 5 | 400-600 | 20-80 | 1-25 | 1000-1,500 | 20-80 |
| 6 | 400-600 | 400-600 | 50-150 | 400-600 | 400-600 |
| 7 | 200-300 | 200-300 | 20-80 | 200-300 | 200-300 |
| 8 | 20-80 | 20-80 | 1-25 | 20-80 | 20-80 |

In a preferred embodiment, the standard set of the present invention, in particular a standard set according to Table 1 and/or Table 2, may comprise two additional calibration standards. The first additional calibration standard preferably contains the same amount of contaminants as the second additional calibration standard, with the second additional calibration standard additionally containing fillers.

A preferred embodiment of these additional calibration standards is illustrated in Table 3.

TABLE 3

| Calibration standard | Cr [ppm] | Br [ppm] | Cd [ppm] | Hg [ppm] | Pb [ppm] |
|---|---|---|---|---|---|
| 1 | 100-500 | 100-500 | 100-500 | 100-500 | 100-500 |
| 2 | 100-500 + fillers | 100-500 + fillers | 100-500 + fillers | 100-500 + fillers | 100-500 + fillers |

The calibration standards are present as molded articles. In general, all molded articles which may be used for testing in an analytical device, preferably an X-ray fluorescence or laser ablation ICP or LIPS device, are suitable.

Preferably, the molded articles are compact molded articles. Preferably, these are present in the shape of a cylinder, a strip, a disc, a sphere or a bulk solid.

In a preferred embodiment, the molded articles have a weight of 0.1 to 100 g (gram), more preferably of 1 g to 30 g. In addition, the molded articles have a surface area of 1 to 10,000 mm², most preferably of 100 to 4,000 mm². The surface should be as planar as possible.

In a particularly preferred embodiment, the molded articles are present in the shape of a cylinder having a diameter of 6 mm to 60 mm and a thickness of 2 to 50 mm (millimeters). The molded article has the shape of a cylinder, with at least one of its sides being planar.

It is also possible that the molded articles are present in the form of granules. In this case, the molded articles are preferably prepared according to the method of the present invention, eliminating step 3b).

Apart from contaminants, the calibration standards may also contain fillers. Fillers mean herein substances that may usually contain polymers for electric and electronic articles. Examples of fillers are flame retardants, reinforcing agents, pigments, flame inhibitors, stabilizers, light stabilizers, antioxidants, inhibitors, catalysts or markers. Further examples are antistatic agents or plasticizers.

Preferably, the added fillers may contain the elements Ba, Al, Ca, Ti, Fe, Cu, Sn and/or Si. If necessary, the fillers may also contain K, Na and/or S.

Examples of substances used as fillers are titanium dioxide, silica, stearates, hindered amine light stabilizers (HALS), calcium carbonate, aluminum hydroxide, antimony trioxide. Further examples are barium sulfate, aluminum silicate, calcium sulfate, magnesium aluminum silicate, calcium oxide and/or carbon blacks.

If the calibration standards contain fillers, these are usually contained in an amount of 1 to 70 weight percent, preferably of 4 to 30 weight percent, based on the total weight of the polymer matrix.

In a preferred embodiment, for example, the following substances are independently contained in the polymer matrix:

$BaCO_3$, usually in an amount of less than 40%, preferably in an amount of 0.01 to 1%;
$Al_2O_3$, usually in an amount of 2 to 45%, preferably in an amount of 5 to 20%;
$SiO_2$, preferably in an amount of 10 to 30%;
$CaCO_3$, usually in an amount of 2 to 50%, preferably in an amount of 5 to 20%;
$TiO_2$, usually in an amount of less than 40%, preferably in an amount of 0.01 to 1%;
Fe, preferably in an amount of 0.01 to 2%;
CuO, usually in an amount of 1 to 15%, preferably in an amount of 1 to 5%;
$SnO_2$, preferably in an amount of 0.1 to 2%;
$Sb_2O_3$, preferably in an amount of 0.1 to 2%;
$BaSO_4$, preferably in an amount of 1 to 50%;

"%" relates herein to the weight percent of the individual substances (i.e. weight percent per amount of, for example, $BaCO_3$ or Fe atoms), based on the total weight of the polymer matrix.

The standard set of the present invention comprising the calibration standards is preferably used for the calibration of a device used in X-ray fluorescence analysis. The standard set of the present invention may also be used for the calibration of laser ablation ICP and laser-induced plasma spectroscopy devices.

In X-ray fluorescence analysis, atoms or ions are irradiated with X-rays; as a result, electrons are separated from the inner shells of the atom. The resulting gaps are filled with electrons from higher shells, with each element emitting X-rays of characteristic wavelengths. These characteristic rays may be used to detect the element composition of the respective sample.

Since the intensity of the irradiation emitted by the sample at a certain wavelength depends on the amount of atoms simultaneously excited to emit these X-rays, the concentration of the respective element in the sample may be inferred from this intensity. As X-ray fluorescence analysis is a relative method, quantitative analysis requires a calibration.

X-rays are in general defined as short-wave electromagnetic radiation of a wavelength ranging from about $10^{-4}$ nm to 10 nm.

Preferably, the calibration standards of the present invention and the standard set of the present invention comprising said calibration standards may be prepared by the below described method of the present invention.

The invention provides a method for manufacturing a calibration standard that consists of a molded article made of a thermoplastic polymer containing the elements Cd, Cr, Pb, Hg and Br (and optionally further of the above mentioned elements).

In a preferred embodiment, the contaminants Cd, Cr, Pb and Hg are present as oxides or sulfates, in particular as oxides. Further forms will be described below for the method of the present invention.

The method of the present invention comprises the following steps:
1) blending a liquid or powder containing the elements Br, Cd, Cr, Pb, Hg with a dispersing agent,
2) blending the dispersion resulting from step 1 with the particulate thermoplastic polymer,
3) extruding the polymer of step 2 to preferably form granules, in particular granules containing the contaminants from the dispersion in a homogeneous distribution.

In general, the contaminants are present as a liquid or powder. In a preferred embodiment, the contaminants are present in the form of a powder containing the elements Cd, Cr, Pb, Hg and a liquid or powder containing the element Br.

In the case of a powder, the elements are preferably present as oxides, sulfates, stearates or halogen-organic compounds. Alternatively, they may also be present as nitrates, sulfides, phosphates, carbonates, salts of organic acids, organic complexes or salts of organic complexes. Preferably, the contaminants Cd, Cr, Pb and Hg are present as oxides or sulfates, in particular as oxides.

The bromine compounds used may be organic or inorganic bromine compounds.

Preferably, the contaminants are present in the form of salts or oxides, in particular in the form of oxides.

Preferably, the bromine compounds are present in the form of organic bromine compounds, more preferably as known bromine-containing flame retardants such as decabromodiphenylethers.

In particular, the following compounds are used:
CdO (cadmium oxide)
Cr (III)-oxide or Cr (IV)-oxide
Pb-stearate
HgO (mercury oxides)

In the method of the present invention, bromine is usually introduced as a liquid or powder, preferably as a powder. In particular, the following Br compound is used: decabromodiphenylether.

In step 1) of the method of the present invention the contaminants are blended with a dispersing agent.

Generally, suitable dispersing agents are liquids that are able to dissolve, suspend or form complexes with the contaminants and are inert towards the polymer. Thus, in a preferred embodiment, the term "dispersing agent" also includes so-called "complexing agents".

Preferably, the dispersing agents used do not disintegrate below 280° C. Further, the dispersing agent preferably has a boiling point of more than 100° C., more preferably of more than 150° C., in particular of more than 200° C. or more than 250° C. Preferably, the dispersing agent is a water-insoluble substance having a viscosity of preferably 100 to 10,000 mPas, in particular of 100 to 7,000 mPas, determined according to DIN 53019 at 25° C.

Examples of suitable dispersing agents may be polyethylene glycoles, waxes and/or polyethers. Further examples are polyimides. Particularly preferred dispersing agents are polyethers.

In step 1 of the method of the present invention the weight ratio of the contaminants (i.e. of a powder containing the elements Cd, Cr, Pb, Hg and of a liquid or powder containing the element Br) to the dispersing agent is usually 0.1 to 10:1, preferably 4 to 2:1.

If the calibration standard to be prepared is to contain fillers, these fillers are preferably also blended with the dispersing agent or added directly as a powder in step 1).

In step 1 of the method of the present invention the weight ratio of the fillers to the dispersing agent is usually 0.1 to 10:1, preferably 2 to 4:1.

In step 2) of the method of the present invention the dispersion resulting from step 1 is blended with the particulate thermoplastic polymer. Step 2) may be performed prior to or during the extrusion. Preferably, step 2) is performed prior to the extrusion.

The blending is usually performed by means of a special blending device, a spatula or a dolly. The blending may be performed over a period of 1 to 120 minutes.

In an alternative embodiment, the contaminants may be added directly to the extruder in liquid form. Preferably, a dosing unit is mounted on the extruder for this purpose. Therefore, in this embodiment, step 2) of the method of the present invention is performed during the extrusion rather than prior to it.

The thermoplastic polymer is used in its particulate form. Examples are polymer granules or polymer powder. Polymer granules are preferred.

In step 3) of the method of the present invention the polymer obtained in step 2) is extruded.

For this process step commercial extruders may be used. Examples of suitable extruders are single-screw extruders such as the Brabender Plasticorder or double-screw extruders (e.g. from Collin, Leistriz, Labtec, etc.).

In general, the extrusion is performed at temperatures from 60 to 400° C., preferably from 60 to 300° C.

In a preferred embodiment, step 3) comprises two substeps.

In a first step 3a), the polymer obtained in step 2 is extruded, preferably to form granules, in particular granules containing the contaminants from the dispersion in a homogeneous distribution.

In a further step 3b), the granules obtained in step 3a) are injection molded—in particular using an injection molding machine—to form a molded article. Preferably, the molded articles have the dimensions described above.

Generally, the preferred embodiments described for the standard set and the calibration standards of the present invention may also be used for the method of the present invention for manufacturing calibration standards.

A final subject of the present invention is a calibration standard prepared by the above described method of the present invention. This calibration standard is characterized, among other things, by an advantageous uniform distribution of contaminants.

Preferably, the calibration standard of the present invention is used for the calibration of an analytical device. In particular, the calibration standard is used for the calibration of an X-ray fluorescence analysis, laser ablation ICP or LIPS device.

"Laser ablation spectroscopy" is an analytical method known in the prior art. The term "laser ablation spectroscopy", as it is used herein, means laser ablation-coupled ICP-MS or ICP-OES. "ICP-MS" is the abbreviation of inductively coupled plasma mass spectrometry. "ICP-OES" means inductively coupled plasma optical emission spectroscopy (for comparison see below).

For a direct analysis (i.e. analysis of solid sample material without prior disintegration) some sample material is separated by means of laser ablation. To this end, a sample is bombarded with a laser beam, thus separating some of the sample, for example in the form of particles, ions, atoms or molecules. This sample material is transported into the plasma via an auxiliary gas stream. The light of the laser beam has usually a wavelength of 190 nm to 1024 nm, preferably of 193 to 266 nm.

Then, the ablated material is supplied to a provocation module such as the ICP, for example by means of a carrier gas stream. Provocation is preferably performed thermally, e.g. in an inductively coupled argon plasma at approx. 7,000 K (Kelvin), resulting in an atomization and ionization or excitation of the sample elements.

In a potential embodiment, the ions generated are detected in a mass spectrometer (MS), preferably after the extraction of the ions from the ICP by means of an interface. Preferably, this interface is a quadrupole mass spectrometer or time-of-flight mass spectrometer or sector-field mass spectrometer. By means of MS ions may be separated and detected according to their mass/charge (m/z) ratio.

In a further potential embodiment, sample elements may be detected by measuring the radiation emitted by these elements. This analytical method is known in the prior art as OES (optical emission spectroscopy).

In X-ray fluorescence analysis atoms or ions are irradiated with X-rays; as a result, electrons are separated from the inner shells of the atom. The resulting gaps are filled with electrons from higher shells, with each element emitting X-rays of characteristic wavelengths. These characteristic rays may be used to detect the element composition of the respective sample. Since the intensity of the irradiation emitted by the sample at a certain wavelength depends on the amount of atoms simultaneously excited to emit these X-rays, the concentration of the respective element in the sample may be inferred from this intensity. X-rays are in general defined as short-wave electromagnetic radiation of a wavelength ranging from about $10^{-4}$ nm to 10 nm.

The LIPS principle (laser-induced plasma spectroscopy) is also often referred to as laser-induced breakdown spectroscopy (LIBS). By means of a pulsed laser, short, intensive light pulses are emitted which are conveyed to the material to be analyzed via a waveguide system. They hit the material in the form of bundled rays, thus "evaporating" minute amounts of the material's surface. Due to the extremely high temperature generated locally by the intensive laser light this is not normal vapor but a so-called plasma. This plasma emits light at certain frequencies which are characteristic for individual chemical elements—so to speak a "fingerprint" of the material. This typical spectrum is analyzed by means of a spectrometer. From the shape of the spectrum the concentration of the individual elements—that is the chemical composition of the material—may be determined. Thus, statements regarding the composition of the liquid, solid or gaseous substance may be made.

The invention will be illustrated by means of the following example.

EXAMPLE

The processing method was performed using 1.5 kg ABS granules and varying contents of the respective elements.

According to Table 4 the following amounts were weighed out:

TABLE 4

| Element compound | Amount weighed out (g) | Corresponds to ppm of the element in 1.5 kg ABS |
|---|---|---|
| $Cr_2O_3$ | 0.1709 | 98.3928 |
| HgO | 0.0149 | 9.1079 |

TABLE 4-continued

| Element compound | Amount weighed out (g) | Corresponds to ppm of the element in 1.5 kg ABS |
|---|---|---|
| CdO | 0.3791 | 218.2605 |
| Decabromodiphenylether | 0.9464 | 520.3181 |
| Pb-stearate | 1.6065 | 546.2100 |

Subsequently, the amounts weighed out were homogeneously blended with approx. 1.3 g polyetherpolyol as dispersing agent in the weighing basin by means of a wooden spatula (step 1). Then, the dispersion including the weighing basin and the wooden spatula was combined with 1.5 kg dried ABS granules in a lidded round 5 l plastic bucket (step 2). To wet the granules with the dispersion, the use of a dolly on which the closed bucket was placed at medium speed in order to blend the dispersion with the granules was suitable. After about one hour the weighing basin and the wooden spatula could be removed and the dispersion had been distributed uniformly on the granules.

Since the elements adhered to the granules uniformly and a contamination by dusts could be excluded, an extrusion was performed (step 3a).

Subsequently, the granules were molded into solid, cylindrical articles fitting in a sample holder of a device used in X-ray fluorescence analysis having a diameter of 3.4 cm by means of an injection molding machine.

First, the cylindrical injection molded articles (pucks) had a diameter of 35 mm and a thickness of 25 mm.

To prepare the cylindrical injection molded articles (pucks), the setting of the injection molding machine was optimized for the respective injection mold. According to Table 5 the following adjustments were performed:

TABLE 5

| Tool temperature: | | 80° C. | |
|---|---|---|---|
| Temperature control: | Draw-in zone | 210° C. | |
| | Zone 2 | 215° C. | |
| | Zone 3 | 215° C. | |
| | Zone 4 | 220° C. | |
| | Nozzle | 225° C. | |
| Injection: | $1^{st}$ stream | 3.0 cm/s | 1860 bar |
| | $2^{nd}$ stream | 3.3 cm/s | 128.0 cm$^3$ |
| | $3^{rd}$ stream | 3.7 cm/s | 213.5 cm$^3$ |
| | | 3.3 cm/s | 5.0 cm$^3$/s |
| Dwell pressure: | $1^{st}$ stream | 1817 bar | 99 s |
| | $2^{nd}$ stream | 1750 bar | 50 s |
| | $3^{rd}$ stream | 1650 bar | 30 s |
| Re-cooling time: | | 450 s | |

The invention claimed is:

1. A standard calibration set comprising at least three calibration standards that contain a molded article made of a thermoplastic polymer which contains the elements Cd, Cr, Pb, Hg and Br, with the Cr:Pb:Hg:Br:Cd weight ratio being different in each of the three calibration standards.

2. The standard set according to claim 1, wherein the polymer is acrylonitrile butadiene styrene or polycarbonate.

3. The standard set according to claim 1, wherein each calibration standard contains at least one of the elements Cr, Pb, Hg and Br in an amount of 0.1 to 500 ppm and at least one of the elements Cr, Pb, Hg and Br in an amount of more than 500 ppm to 2,000 ppm, wherein at least one calibration standard contains Cd in an amount of 0.1 to 50 ppm and at least one calibration standard contains Cd in an amount of more than 50 ppm to 200 ppm, based on the total weight of the polymer.

4. The standard set according to claim 1, wherein the molded article has the shape of a cylinder.

5. The standard set according to claim 1, wherein the standard set comprises a number of at least 8 calibration standards.

6. The standard set according to claim 1, wherein at least one calibration standard contains one or more fillers, with the fillers being compounds containing the elements Ba, Al, Li, Ca, Ti, Fe, Cu, Sn, Sb and/or Si.

7. The standard set according to claim 6, wherein the amount of fillers ranges from 1 to 70 weight percent, based on the total weight of the calibration standard.

8. The standard set according to claim 1, wherein each of the calibration standards is independently prepared by the steps of
1) blending a liquid or a powder containing the elements Br, Cd, Cr, Pb, Hg with a dispersing agent,
2) blending the dispersion resulting from step 1 with a particulate thermoplastic polymer,
3) extruding and molding the polymer of step 2.

9. A method for the calibration of an analytical device, said method comprising calibrating said device with the calibration set of claim 1.

10. The method of claim 9, wherein each of the calibration standards is independently prepared by the steps of
1) blending a liquid or a powder containing the elements Br, Cd, Cr, Pb, Hg with a dispersing agent,
2) blending the dispersion resulting from step 1 with a particulate thermoplastic polymer,
3) extruding and molding the polymer of step 2.

11. The method of claim 9, wherein the device is an X-ray fluorescence analysis or laser ablation inductively coupled plasma or laser-induced plasma spectroscopy device.

12. The method of claim 9, further comprising deciding upon a number n of elements for which the device is to be calibrated, and preparing the calibration set with at least $2n+2$ calibration standards.

13. A method for manufacturing a calibration standard containing a molded article made of a thermoplastic polymer which contains the elements Cd, Cr, Pb, Hg and Br, comprising the steps of
1) blending a liquid or a powder containing the elements Br, Cd, Cr, Pb, Hg with a dispersing agent,
2) blending the dispersion resulting from step 1 with a particulate thermoplastic polymer,
3) extruding and molding the polymer of step 2.

14. The method according to claim 13, wherein the dispersing agent is a water-insoluble substance.

15. The method of claim 14, wherein the dispersing agent has a viscosity of 200 to 7,000 mPas, measured according to DIN 53019 at 25° C.

16. The method according to claim 13, wherein the dispersing agent has a boiling point of more than 150° C.

17. The method according to claim 13, wherein in step 1 the weight ratio of the liquid or powder containing the elements Br Cd, Cr, Pb, Hg to the dispersing agent is 0.1 to 10:1.

18. The method according to claim 13, wherein in step 1 the elements Cd, Cr, Pb, Hg and Br are present in the form of cadmium oxide, chromium oxide, lead oxide, mercury oxide and polybromated diphenylethers.

19. The method according to claim 13, wherein in step 1, additional fillers, which contain the elements Ba, Al, Li, Ca, Ti, Fe, Cu, Sn, Sb and/or Si, are blended with the dispersing agent.

20. The method according to claim 19, wherein in step 1 the fillers/dispersing agent weight ratio is 0.1 to 10:1.

\* \* \* \* \*